(12) United States Patent
Lemaitre et al.

(10) Patent No.: US 7,407,542 B2
(45) Date of Patent: Aug. 5, 2008

(54) PASTY OR LIQUID MULTIPLE CONSTITUENT COMPOSITIONS FOR INJECTABLE CALCIUM PHOSPHATE CEMENTS

(75) Inventors: Jacques Lemaitre, Lausanne (CH); Christian Pittet, Chavannes-Renens (CH); David Brendlen, Ecublens (CH)

(73) Assignee: Ecole Polytechnique Federale de Lausanne - Service des Relations Industrielles

( * ) Notice: Subject to any disclaimer, the term of this patent is extended or adjusted under 35 U.S.C. 154(b) by 120 days.

(21) Appl. No.: 10/491,189

(22) PCT Filed: Oct. 1, 2002

(86) PCT No.: PCT/CH02/00543

§ 371 (c)(1),
(2), (4) Date: Mar. 31, 2004

(87) PCT Pub. No.: WO03/041753

PCT Pub. Date: May 22, 2003

(65) Prior Publication Data

US 2004/0244651 A1   Dec. 9, 2004

(30) Foreign Application Priority Data

Nov. 14, 2001   (CH) ..................... 2086/01

(51) Int. Cl.
*C04B 12/02* (2006.01)
*C09K 3/00* (2006.01)

(52) U.S. Cl. ......................... 106/35; 106/690
(58) Field of Classification Search ................ 106/690, 106/35

See application file for complete search history.

(56) References Cited

U.S. PATENT DOCUMENTS

| 4,288,355 A | * | 9/1981 | Anderson et al. ........... 523/116 |
| 4,678,436 A | * | 7/1987 | Kondo et al. ............. 433/228.1 |
| 5,129,905 A | | 7/1992 | Constantz |
| 5,496,399 A | | 3/1996 | Ison et al. |
| 5,505,538 A | * | 4/1996 | Earle .......................... 366/139 |
| 5,522,893 A | | 6/1996 | Chow et al. |
| 6,149,655 A | | 11/2000 | Constantz et al. |
| 6,642,285 B1 | * | 11/2003 | Bohner ....................... 523/115 |

FOREIGN PATENT DOCUMENTS

| EP | 0 976 443 | 7/1999 |
| WO | WO 98/15314 | 4/1998 |
| WO | WO 99/17710 | 4/1999 |
| WO | WO 01/41824 | 6/2001 |

* cited by examiner

*Primary Examiner*—Elizabeth D Wood
(74) *Attorney, Agent, or Firm*—Nixon & Vanderhye P.C.

(57) ABSTRACT

The invention concerns injectable bone filling cements, in particular hydraulic calcium phosphate cements, the latter being prepared from at least two initial liquid or pasty constituents comprising each a species reactive in solution or in suspension, the solidification process being initiated when said constituents are being mixed.

10 Claims, No Drawings

PASTY OR LIQUID MULTIPLE CONSTITUENT COMPOSITIONS FOR INJECTABLE CALCIUM PHOSPHATE CEMENTS

This application is the US national phase of international application PCT/CH02/00543 filed 1 Oct. 2002 which designated the U.S. and claims benefit of CH 2086/01, dated 14 Nov. 2001, the entire contents of each of which are hereby incorporated by reference.

TECHNICAL FIELD

The present invention relates to injectable bone filling cements, more particularly calcium phosphate hydraulic cements.

STATE OF THE ART

Injectable bone filling cements exist in two highly distinct forms: acrylic cements, which harden by a polymerization reaction, and calcium phosphate hydraulic cements (CPHC), which harden by a dissolution and precipitation reaction of entities comprising phosphates and/or calcium cations.

The CPHC cements to which the present invention relates harden from the moment when one or more dry powders is/are mixed with a certain amount of a liquid constituent. This implies that there are at least two starting constituents and that the time is counted from the moment when these constituents are mixed, as the setting reaction is activated and the paste thus obtained begins to harden until a solid body is formed.

The small amount of time available for the mixing, and the need to carry out this mixing under sterile conditions, have forced manufacturers of bone filling cements to provide mechanical mixing systems. These systems exhibit the advantage of better reproducibility of the qualities of the cement obtained and increased ease of use (in comparison with mixing carried out by hand). However, the systems developed are often complicated, unwieldy and relatively expensive. This complexity arises mainly from the fact that the production of a homogeneous mixture from a dry powder and a liquid is a difficult operation. A mixing system for calcium phosphate cements has been provided in Patent EP 0 976 443. The latter makes possible the production of a paste with a solid/liquid ratio identical to that of the amounts mixed (all the powder is effectively mixed), which difficulty the system of Patent WO 98/15314 has not overcome, according to the inventors of Patent EP 0 976 443. Another mixing system, for Norian SRS® cement, had been patented (U.S. Pat. No. 6,149,655) but it clearly proves the difficulty of obtaining a homogeneous paste from a powder and a liquid since it recommends repeating the mixing movement 60 to 90 times before a homogeneous paste is obtained. A large number of mixing systems have been patented for acrylic cements too but they are also complicated and unwieldy.

The systems developed to date for bone filling cements are therefore complicated, unwieldy and relatively expensive and exhibit a mixing stage separate from the injection stage.

The present invention provides in particular a novel process for the preparation and injection of cement. This process makes it possible to reduce the operations in which the cement paste is handled and to reduce the time between the moment of mixing and the moment of injection. This is possible by mixing two liquid or pasty constituents which each comprise a reactive entity, because the time necessary for the production of a homogeneous paste from two pastes or liquids is much shorter than from a powder and a liquid as the stage of wetting the powders is already carried out at the moment when the pastes are mixed. The present process thus provides for the presentation of the starting constituents of calcium phosphate hydraulic cements in the form of liquids or pastes.

Furthermore, by carrying out a preliminary degassing of the liquid or pasty constituents, the process according to the invention makes it possible to obtain a deaerated cement which is more compact in comparison with the calcium phosphate cements of the state of the art.

ACCOUNT OF THE INVENTION

The present invention relates to the presentation of a calcium phosphate cement in the form of at least two liquid or pasty starting constituents, each comprising a reactive entity in solution or in suspension. Said constituents do not precipitate and therefore do not form a cement as long as they are not mixed, the precipitation reaction only occurring during the mixing of said constituents.

This presentation in the liquid or pasty form makes possible, for example, the ready use of the injectable product in dentistry or in surgery, for example using a syringe or a twin-chambered gun which comprises a common passage for the mixing of the constituents.

This presentation allows the clinician to dispense with the manual mixing stage since it makes it possible to simultaneously carry out the mixing and the injection by simple action on a piston or a trigger. Furthermore, dispensing with the conventional manual mixing with a spatula makes it possible to avoid the incorporation of air bubbles in the paste, the latter being harmful to the mechanical properties of the cement. In order to render the hardened cement as compact as possible and to provide mechanical properties which are as reproducible as possible, the liquids or pastes can be degassed at the moment of their preparation.

The advantage of mixing two liquid or pasty constituents lies in the fact that the mixing can be carried out during the injection, which limits the stages, and the operations in which the cement is handled.

It is possible to apply the present invention to any type of calcium phosphate cement, the reactions for the synthesis of cement being used to determine the reactive entities to be used. Many such reactions are found in the literature and in particular in the publication: J. Lemaitre, "Injectable calcium phosphate hydraulic cements: new developments and potential applications", Inn. Technol. Biol. Med., Vol. 16 (Sp. No. 1), 109, 1995.

Mention may in particular be made of the cements of brushite type which can be used. The latter are obtained from mixtures of tricalcium phosphate and of monocalcium phosphate monohydrate and of other calcium or sodium salts which are not very soluble in an aqueous medium.

Depending on the duration of stability desired for the liquid or pasty constituents, a person skilled in the art will choose the reaction conditions for which the reactive entities exhibit the desired stability in solution. This is because a person skilled in the art knows how to calculate the stability of the reactive substances in aqueous solutions by applying, for example, the calculations of solubility of phosphates in an aqueous medium set out in the publication: G. Vereecke and J.

Lemaitre, "Calculation of solubility diagrams in the system $Ca(OH)_2$—$H_3PO_4$—$KOH$—$HNO_3$—$CO_2$—$H_2O$", Journal of Crystal Growth, Vol. 104, 820, 1990.

EMBODIMENTS

EXAMPLE 1

Calcium phosphate cement of brushite type presented in the form of two pasty starting constituents.

The reaction which takes place at the moment of the mixing of the two pastes is as follows:

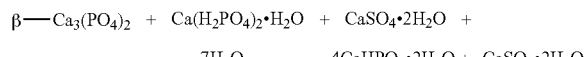
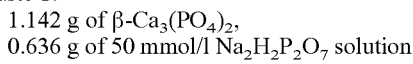

The pastes can be provided in the following way:
Paste 1:
  1.142 g of β-$Ca_3(PO_4)_2$,
  0.636 g of 50 mmol/l $Na_2H_2P_2O_7$ solution
Paste 2:
  0.743 g of $Ca(H_2PO_4)_2.H_2O$,
  0.322 g of $CaSO_4.2H_2O$,
  0.514 g of water.

Plaster $CaSO_4.2H_2O$ participates in the composition of Paste 2 for ancillary reasons (retarding the setting of the cement, better tolerance of the cement in vivo, and the like).

It is possible to add, to Paste 1 or 2 or to both, polymeric adjuvants, suspension stabilizers, setting retardants (for example $Na_2H_2P_2O_7$), radiopaques, for example based on iodine, or medicines (antibiotics, antimitotics, agents for promoting bone regrowth, and the like).

EXAMPLE 2

Calcium phosphate cement of the type of Example 4 of U.S. Pat. No. 5,522,893 (WO 94/20064) of Chow and Takagi.

The reaction which takes place at the moment of mixing of the two pastes is as follows:

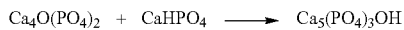

The pastes can be provided in the following way:
Paste 1:
  3.66 g of $Ca_4O(PO_4)_2$,
  1.85 g of sterile water,
Paste 2:
  1.36 g of $CaHPO_4$,
  2.30 g of $Ca_5(PO_4)_3OH$,
  1.85 g of 10 mmol/l orthophosphoric acid.

EXAMPLE 3

Apatitic calcium phosphate cement of Norian SRS® type. This type of cement is disclosed in U.S. Pat. No. 5,129,905. The reaction which takes place at the moment of the mixing of the two pastes is as follows:

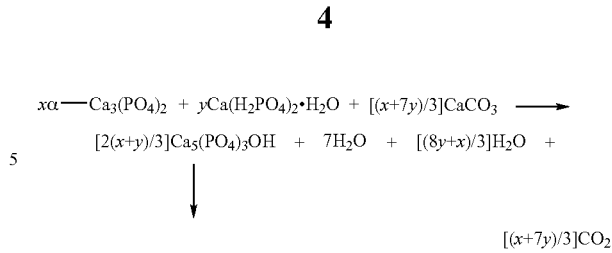

The pastes can be provided in the following way:
Paste 1:
  1.53 g of α-$Ca_3(PO_4)_2$,
  0.31 g of $CaCO_3$,
  0.90 g of 100 mmol/l $Na_2HPO_4$,
Paste 2:
  0.16 g of $Ca(H_2PO_4)_2.H_2O$,
  1.68 g of $Ca_5(PO_4)_3OH$,
  0.80 g of 10 mmol/l orthophosphoric acid.

The cements obtained according to the method of the invention are denser than those obtained by the conventional methods involving one or more dry powders mixed with a liquid constituent. This is the result of the degassing of the starting liquids/pastes, which stage is impossible in the known methods as the necessary time is not available.

Like Example 1, it is possible to add various substances to the pastes of Examples 2 and 3.

What is claimed is:

1. A process for making a calcium phosphate cement from a reaction of at least two pasty starting constituents which are mixed together in a mixing step, each of said constituents containing at least one reactive entity; said process also comprising a degassing step which is carried out on each constituent before the mixing step.

2. The process as claimed in claim 1, wherein the pasty constituents comprise aqueous solutions of at least one of the following compounds: di-sodium di-hydrogen pyrophosphate ($Na_2H_2P_2O_7$), di-sodium hydrogen orthophosphate ($Na_2HPO_4$), and orthophosphoric acid ($H_3PO_4$).

3. The process as claimed in claim 1, wherein the calcium phosphate cement is DCPD (dicalcium phosphate dihydrate) and the reactive entities are β-TCP (β-tricalcium phosphate) and MCPM (monocalcium phosphate monohydrate).

4. The process as claimed in claim 1, wherein the calcium phosphate cement is OHAP (hydroxyapatite) and the reactive entities are TTCP (tetracalcium phosphate monoxide) and DCPA (anhydrous dicalcium phosphate).

5. The process as claimed in claim 1, wherein the calcium phosphate cement is OHAP (hydroxyapatite) and the reactive entities are α-TCP (α-tricalcium phosphate), MCPM (monocalcium phosphate monohydrate) and CC (calcium carbonate).

6. The process as claimed in claim 1, wherein polymeric adjuvants and/or suspension stabilizers and/or setting retardants and/or radiopaques and/or medicines are added to one or to several of the reactive entities in paste form.

7. A cement, obtained by the process as claimed in claim 1.

8. The process as claimed in claim 1, wherein said reactive entities are introduced into a multicompartment device, and a mixing system is used for bringing said reactive entities into contact.

9. A method of preparing a calcium phosphate cement for use in surgery or dentistry comprising:
  a) providing two reactive entities which are each in paste form,
  b) degassing the two reactive entities and then
  c) mixing said entities to form the calcium phosphate cement.

10. A calcium phosphate cement produced from combining and reacting at least two pasty constituents wherein each constituent of at least two pasty constituents comprise one or more reactive entities and the pasty constituents are degassed prior to combining and reacting.

* * * * *